United States Patent [19]

Lampi et al.

[11] Patent Number: 5,237,094
[45] Date of Patent: Aug. 17, 1993

[54] PROCESS FOR THE PREPARATION OF METHYLENEBISPHOSPHONIC ACIDS

[75] Inventors: Klaus Lampi, Turku; Kauko Nieminen, Masku; Jarkko Ruohonen, Vanhalinna, all of Finland

[73] Assignee: Leiras Oy, Turku, Finland

[21] Appl. No.: 838,422

[22] PCT Filed: Aug. 15, 1990

[86] PCT No.: PCT/FI90/00197
§ 371 Date: Apr. 30, 1992
§ 102(e) Date: Apr. 30, 1992

[87] PCT Pub. No.: WO91/03480
PCT Pub. Date: Mar. 21, 1991

[30] Foreign Application Priority Data

Sep. 8, 1989 [FI] Finland .................. 894245

[51] Int. Cl.$^5$ .................. C07F 9/38
[52] U.S. Cl. .................. 562/22
[58] Field of Search .................. 562/22

[56] References Cited

U.S. PATENT DOCUMENTS 4,621,077 11/1986 Rosini et al. .................. 514/108

FOREIGN PATENT DOCUMENTS 0200980 11/1986 European Pat. Off. .
0230068 7/1987 European Pat. Off. .
2229087 12/1973 Fed. Rep. of Germany .
1026366 4/1966 United Kingdom .

OTHER PUBLICATIONS

Houben-Weyl, Methoden der Organischen Chemie, XII, 1, 352-356 (1963).
Morrison & Boyd, Organic Chemistry, 5th Ed., p. 875, (1959).

Primary Examiner—Robert W. Ramsuer
Attorney, Agent, or Firm—Wolf, Greenfield & Sacks

[57] ABSTRACT

The present invention concerns a novel process for the preparation of methylenebisphosphonic acids of the formula I

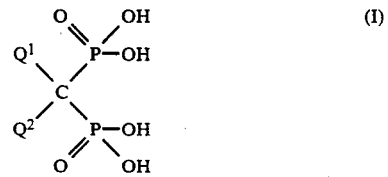

wherein $Q^1$ and $Q^2$ are independently hydrogen or halogen, by hydrolyzing the corresponding methylenebisphosphonic acid tetraester of the formula

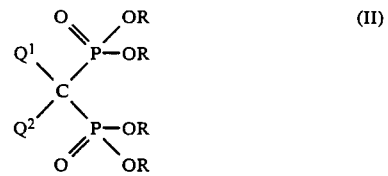

wherein R has the meaning of a straight or branched alkyl group containing 1 to 4 carbon atoms, and $Q^1$ and $Q^2$ have the same meaning as above.

6 Claims, 1 Drawing Sheet

PROCESS FOR THE PREPARATION OF METHYLENEBISPHOSPHONIC ACIDS

BACKGROUND OF THE INVENTION

The present invention concerns a novel process for the preparation of methylenebisphosphonic acids of the formula I

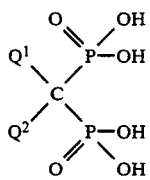

wherein $Q^1$ and $Q^2$ are independently hydrogen or halogen, by hydrolyzing the corresponding methylenebisphosphonic acid tetraester of the formula

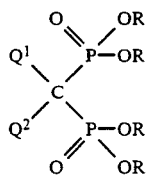

wherein R has the meaning of a straight or branched alkyl group containing 1 to 4 carbon atoms, and $Q^1$ and $Q^2$ have the same meaning as above.

Prior known processes for the preparation of bisphosphonic acids by hydrolyzing the corresponding tetraesters have been based on the use of strong acids, such as halogen acids. Thus tetraesters, e.g. the isopropyl tetraester, have been boiled for several hours with concentrated hydrochloric acid (c.f. BE-patent 672205, example VI (B)). In the publication Houben-Weyl, Methoden der Organischen Chemie, XII, 1, 352–356, the hydrolysis of tetraesters with half-concentrated hydrochloric acid under elevated pressure and at 130°–145° C. is described. A disadvantage with these known processes is the impurity of the products obtained and the numerous purification steps needed to remove byproducts and excess acid. In addition, the processes are connected with substantial corrosion problems. From the EP-patent application 0200980 is known a process according to which methylenebisphosphonic acids have been prepared by hydrolysing tetraesters with plain water, by boiling at reflux temperature of the reaction mixture. In this case the above mentioned problems of impurities and corrosion are largely overcome, but another problem is the very long reaction time, which may be as long as 16 hours, which is disadvantageous, i.a. from the viewpoint of production economics.

SUMMARY OF THE INVENTION

Now a process has been invented for the preparation of the above mentioned methylenebisphosphonic acids and their salts according to the formula I, with a good yield and in a very pure form, whereby the corrosion problems caused by the use of a strong acid are avoided. By means of the process according to the invention it has also been possible to shorten the reaction time even up to one quarter or more as compared to the process known from the EP-patent application 0200980.

The process according to the invention is thus characterized in that the hydrolysis is performed in an aqueous solution of the tetraester and hydrochloric acid, which solution contains from 1.0 to 5% by weight of HCl, based on the whole mixture. Below the said limit the hydrolysis proceeds too slowly from a practical viewpoint and above the said limit no substantial rate increase is achieved in relation to the amount of chloride ions added to the mixture.

DETAILED DESCRIPTION

Figure 1:
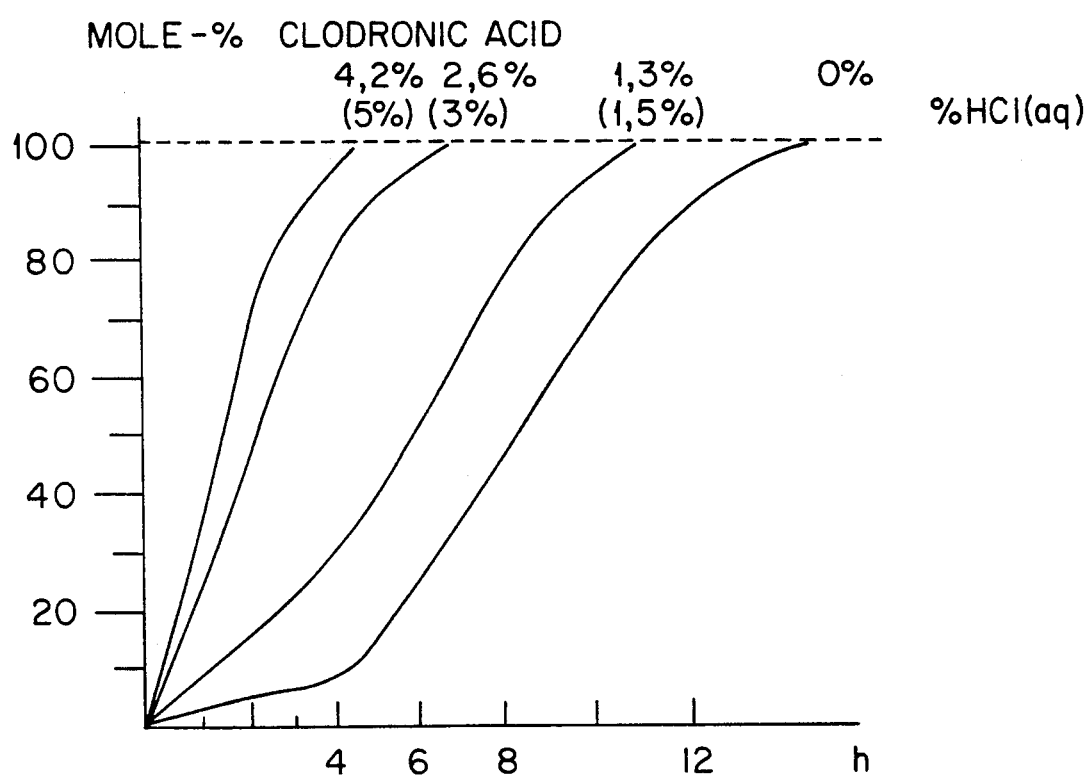
FIG. 1 is a graph of the yield of hydrolysis (mole percent free acid) versus reaction time in hours, of three hydrolysis mixtures of this invention compared to plain water according to the prior art.

The hydrolysis is advantageously performed by boiling the aqueous solution of the tetraester and hydrochloric acid at reflux temperature. Thus the reaction mixture contains an excess of water with regard to the stochiometric amount of water necessary for the complete hydrolysis of the tetraester. This excess of water is not critical and thus a multiple excess with regard to the stochiometric amount may be used. A practical volumetric amount of aqueous hydrochloric acid solution from the viewpoint of carrying out the hydrolysis is approximately 6 to 7 times the weight of the tetraester, whereby, on the one hand, a sufficient degree of dissolution of the tetraester in the aqueous medium is obtained, but at the same time the difficulties caused by the increase in volume in the subsequent hydrolysis stage are avoided.

According to one advantageous embodiment the amount of hydrochloric acid in the mixture is approximately 2.5 to 5% by weight, whereby an optimal result from the viewpoint of byproduct formation and reaction time is achieved.

The free tetraacid obtained as a result of the hydrolysis may, if desired, be converted to its salt, also its partial salt, in a per se known manner by using a suitable organic or inorganic base, for example alkali or alkaline earth metal hydroxides, carbonates or hydrogen carbonates. The salt formation may take place either after the isolation of the acid or by adding the desired base directly to the reaction mixture after the hydrolysis, without isolating the free acid.

The following example illustrates the invention.

EXAMPLE 1

Dichloromethylenebisphosphonic acid disodiumtetrahydrate

Into a three-necked flask equipped with a thermometer, a stirrer and a reflux condenser, 420 ml of a 3% hydrochloric acid solution and 65 g of tetraisopropyl dichloromethylenebisphosphonate are added. The HCl-concentration of the reaction mixture is then approximately 2.6% by weight of HCl. The mixture is boiled under reflux and the progress of the hydrolysis is followed by determining the concentration of the acid formed in the solution by $^{31}$P-NMR. The solution is cooled to 20° to 25° C. and is treated with activated carbon. To the solution a calculated amount of a sodium hydroxide solution is added until the pH is 3.2. The solution is concentrated and cooled, whereby the disodiumtetrahydrate salt of dichloromethylenebisphosphonic acid crystallizes. The crystals are filtered and dried, whereby appr. 50 g of the product is obtained, purity >99%.

By performing the hydrolysis as described above but by using instead of the 3% hydrochloric acid solution, aqueous hydrochloric acid solutions of varying strength, the hydrolysis results shown in the appended drawing were obtained. Next to each curve on the one hand the acid strength of the hydrolysis mixture, and on the other hand, in parenthesis, the acid strength of the aqueous hydrochloric acid solution used, are indicated. In the drawing the yield of hydrolysis (mol-% free acid) are indicated as a function of reaction time, and as comparison, hydrolysis with plain water according to the EP-patent application 0200980 is used. As is seen from the drawing, complete yields are obtained with the process according to the invention, by using catalytic amounts of hydrochloric acid, in a substantially shorter reaction time as compared to the process according to the said EP-patent application.

We claim:

1. A process for the preparation of methylenebisphonic acids of the formula I

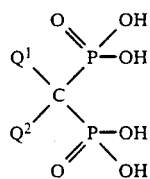

(I)

wherein $Q^1$ and $Q^2$ are independently hydrogen or halogen, consisting essentially of hydrolyzing the corresponding methylenebisphosphonic acid tetraester having the formula II

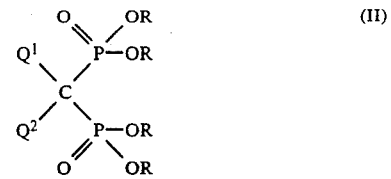

(II)

wherein R is selected from the group consisting of straight and branched alkyl groups of 1 to 4 to carbon atoms and $Q^1$ and $Q^2$ are independently selected from the group consisting of hydrogen and halogen, wherein the hydrolysis is performed in a hydrolysis mixture of the tetraester and an aqueous hydrochloric acid solution, which mixture contains 1.0 to 5% by weight of hydrochloric acid.

2. The process of claim 1, further comprising converting the free tetraacid obtained to a salt with a base.

3. The process of claim 1, wherein a 6 to 7-fold volumetric amount of an aqueous hydrochloric acid solution is used compared to the weight of the tetraester.

4. The process of claim 1, wherein the hydrolysis is performed by boiling at the reflux temperature of the mixture.

5. The process of claims 6 2, 3, or 4, wherein the hydrolysis mixture contains 2.5 to 5% by weight of hydrochloric acid.

6. The process of claim 1, wherein the tetraester of formula II is the tetraisopropylester of dichloromethylenebisphosphonic acid.

* * * * *

UNITED STATES PATENT AND TRADEMARK OFFICE
CERTIFICATE OF CORRECTION

PATENT NO. : 5,237,094
DATED : August 17, 1993
INVENTOR(S) : Lampi, et. al.

It is certified that error appears in the above-indentified patent and that said Letters Patent is hereby corrected as shown below:

On the Title page, item [57], delete the Abstract and insert the following:

-- The object of the invention is a process for the preparation of optionally mono- or dihalogen substituted methylenebisphosphonic acids, whereby the corresponding lower alkyl tetraester is hydrolyzed in an aqueous solution of the tetraester and hydrochloric acid, which solution contains 1 to 5% by weight of HCl, calculated on the mixture. --

Signed and Sealed this

Fifteenth Day of March, 1994

*Attest:*

BRUCE LEHMAN

*Attesting Officer*    *Commissioner of Patents and Trademarks*